United States Patent
Hansen

Patent Number: 5,161,283
Date of Patent: Nov. 10, 1992

[54] METHOD AND APPARATUS FOR FORMING AN ABSORPTION BODY BY USING VARIABLE SUBPRESSURE AS FIBERS ARE DRAWN

[75] Inventor: Kjell Hansen, Jersoy, Norway

[73] Assignee: Molnlycke AB, Gothenburg, Sweden

[21] Appl. No.: 684,945

[22] PCT Filed: Nov. 14, 1989

[86] PCT No.: PCT/SE89/00657
§ 371 Date: Apr. 26, 1991
§ 102(e) Date: Apr. 26, 1991

[87] PCT Pub. No.: WO90/05511
PCT Pub. Date: May 31, 1990

[30] Foreign Application Priority Data

Nov. 15, 1988 [SE] Sweden ............... 8804119

[51] Int. Cl.⁵ .......... D01G 25/00; A61F 13/20
[52] U.S. Cl. .................... 19/148; 28/118; 28/119; 264/517
[58] Field of Search .......... 28/118, 119; 19/148, 19/304, 308; 264/517, 518; 425/80.1

[56] References Cited

U.S. PATENT DOCUMENTS

| | | |
|---|---|---|
| 3,177,275 | 4/1965 | Brenner ............... 19/148 |
| 3,717,905 | 2/1973 | Furbeck ............... 19/148 |
| 4,592,708 | 6/1986 | Feist et al. ............... 264/517 |
| 4,627,953 | 12/1986 | Johnson . |
| 4,666,647 | 5/1987 | Enloe et al. ............... 19/308 X |
| 4,904,440 | 2/1990 | Angstadt ............... 264/518 X |
| 4,995,141 | 2/1991 | Gould ............... 19/148 |

FOREIGN PATENT DOCUMENTS

| | | |
|---|---|---|
| 0000222 | 1/1979 | European Pat. Off. . |
| 0455467 | 7/1988 | Sweden . |
| 2010934 | 7/1979 | United Kingdom ............ 19/148 |

Primary Examiner—Werner H. Schroeder
Assistant Examiner—Bibhu Mohanty
Attorney, Agent, or Firm—Young & Thompson

[57] ABSTRACT

To produce an absorption body, a mold having an air-permeable bottom is filled progressively with airborne fibers of absorbent material and subpressure is applied through the air-permeable mold bottom. This subpressure is varied progressively and directly as the thickness of the absorption body progressively increases as the mold is progressively filled with fibers. Thus, the amount of air drawn through the absorption body by the subpressure remains substantially constant despite progressive increase in the thickness of the body. The result is an absorption body having substantially constant density throughout its thickness.

10 Claims, 3 Drawing Sheets

METHOD AND APPARATUS FOR FORMING AN ABSORPTION BODY BY USING VARIABLE SUBPRESSURE AS FIBERS ARE DRAWN

The present invention relates to a method and to apparatus for forming an absorption body, wherein a mould having an air-permeable bottom is filled successively with airborne cellulose-fibres or fibres of some other absorbent material, with the assistance of subpressure, and wherein the absorption body formed in the mould is then pressed-out of the mould with the aid of overpressure.

It is normal practice in the technical field to which this invention pertains to utilize a subpressure for the purpose of filling moulds with absorbent material, by introducing a mixture of air and loose cellulose-fibres or the like into the mould and causing the air to pass through the mould bottom while depositing the fibres in the mould. Because the layers of fibre deposits are air-permeable in themselves, it is possible to deposit successive layers of fibres in this manner until the mould is full.

Swedish Patent Document 455,467 discloses an apparatus of this kind in which a vacuum box for creating a subpressure under a mould is divided into several separate compartments. Each compartment has means for controlling the subpressure and it is known from this publication to have subpressures in the compartments, which are increasing from compartment to compartment as a mould travels past the vacuum box. The filling of the mould is effected during the travel of the mould past the first compartment and the subpressures in the subsequent compartments is chosen for creating a suitable thickness and density of the fiber body in the mould.

In the present day manufacture of absorbent products, such as disposable diapers, incontinence guards, etc., it is a constant endeavour to use thinner and thinner absorption bodies, without losing the absorbency or absorption capacity afforded by the thicker absorption bodies which the thinner absorption bodies are intended to replace. This endeavour can be achieved, inter alia, by imparting different densities to different parts of the absorption bodies, which, among other things, results in improved liquid dispersion and consequently enables a greater part of the available absorption capacity of the body to be utilized more effectively. In this case, the absorption body may be formed from two discrete sub-bodies of mutually different densities, or may consist of a single entity having mutually different densities in different parts thereof.

Consequently, in order to ensure that the progressively more sophisticated configuration of such absorption bodies will actually have the effect intended, progressively higher demands are placed on the homogenity of the cellulose-fluff body produced, this body constituting the starting product on which further manufacturing processes are based.

The object of the present invention is to provide a method and apparatus for forming an absorption body whose mass of cellulose-fluff or corresponding material is essentially homogenous.

Accordingly, a method of the kind described in the introduction is characterized by varying the subpressure beneath the mould bottom in response to the variation in resistance to air-flow of the mould bottom and the cellulose-fluff which collects progressively in the mould. As a result, the air-flow through the mould can be maintained substantially constant and, correspondingly, the number of cellulose-fibres deposited in the mould per unit of time will also be essentially constant and compaction of the various parts of the body will be uniform. In the formation of homogenous absorption bodies, the inventive method enables the apparatus required to put the method into effect to be of simple and uncomplicated construction.

Accordingly, the invention also relates to apparatus for forming an absorption body, comprising a mould having an air-permeable bottom, means for supplying a mixture of air and loose fibres to the surroundings externally of the mould, a subpressure source for creating a subpressure beneath the mould and means for varying the subpressure beneath the mould, the apparatus including a pressure chamber located beneath the bottom of the mould characterized in that means for varying the subpressure beneath the mould comprise a variable opening connecting the pressure chamber to the pressure source.

So that the invention will be understood more readily, a preferred embodiment of the invention will now be described with reference to the accompanying drawings, of which:

Figure 1:
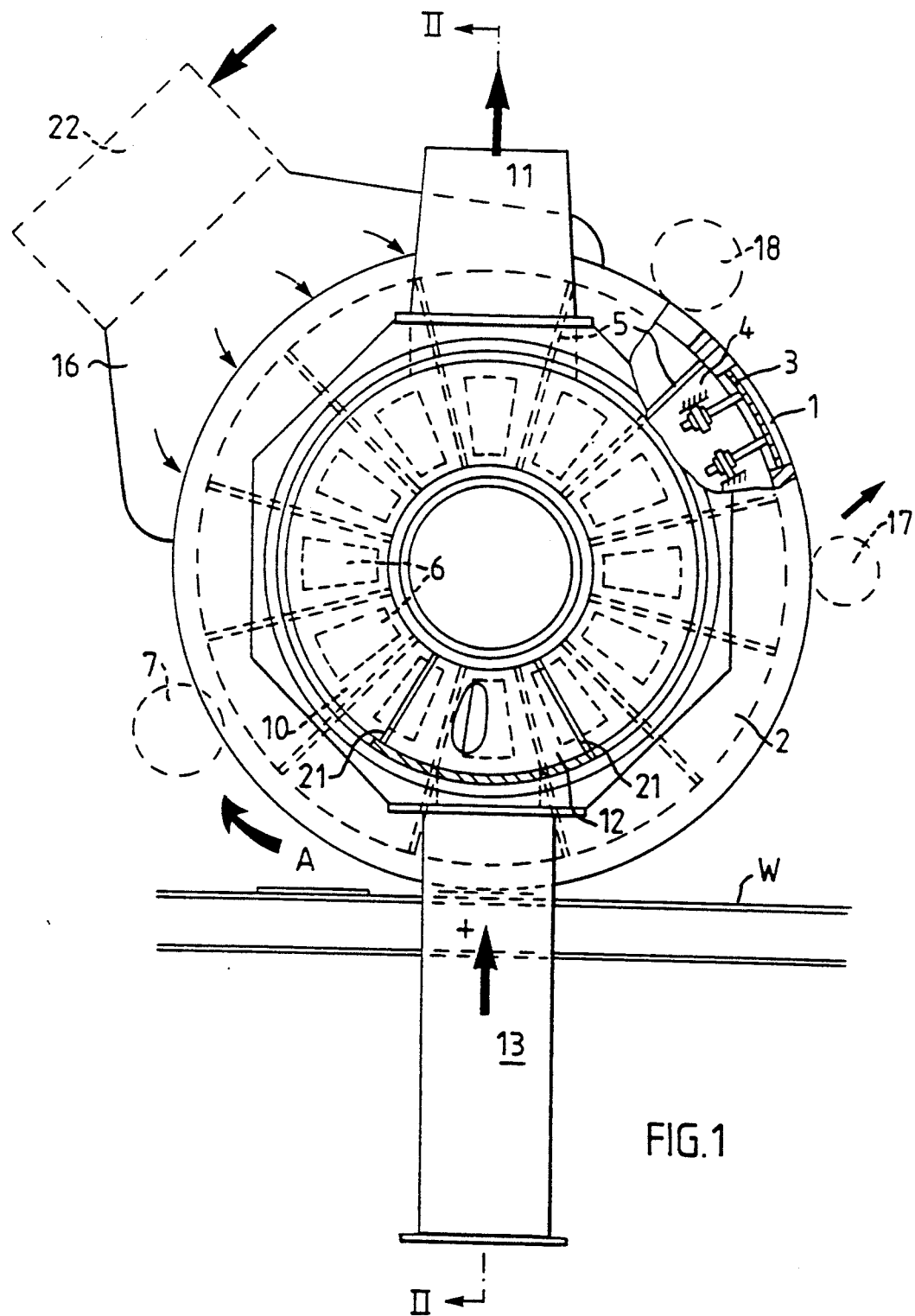
FIG. 1 illustrates an inventive apparatus in side-view and partly in section.
Figure 2:
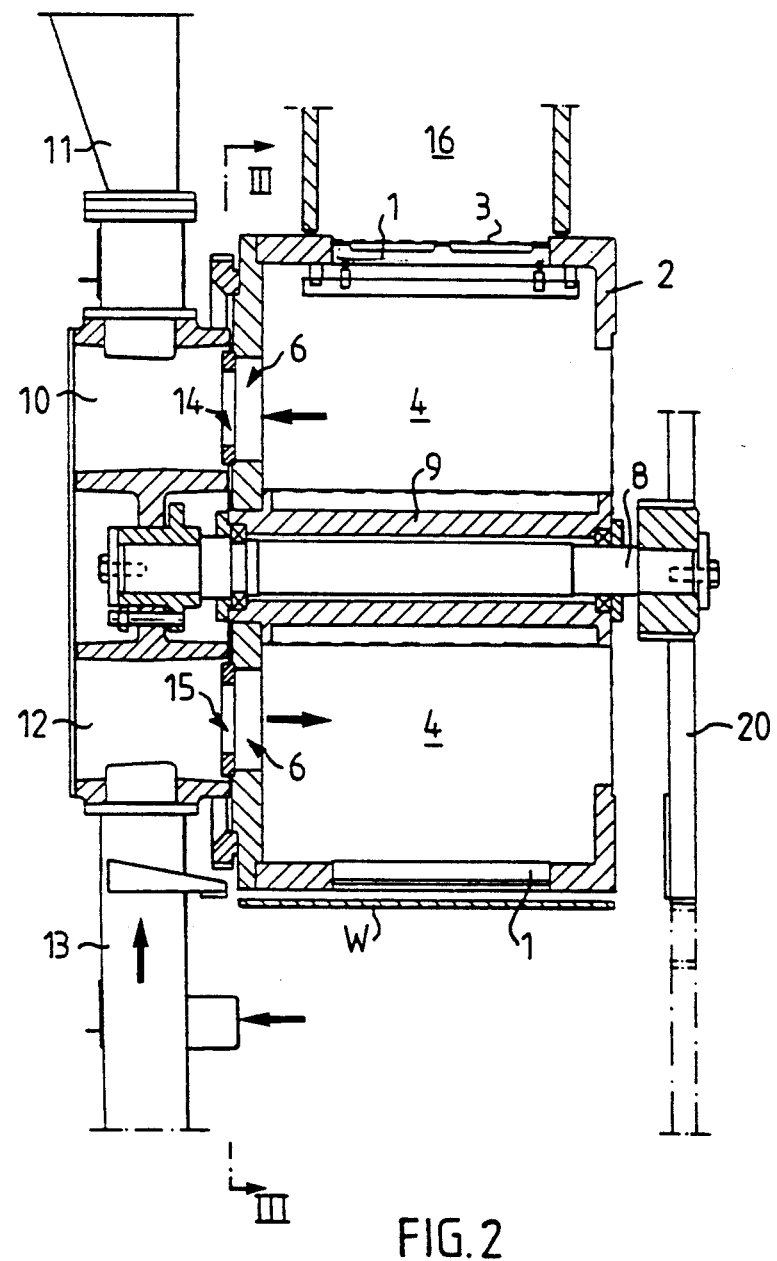
FIG. 2 is a cross-sectional view taken on the line II—II in FIG. 1.

FIGS. 1 and 2 illustrate a preferred embodiment of the invention in which a plurality of moulds 1 intended to receive cellulose-fluff are disposed uniformly around the circumference of a mould-wheel 2, which is journalled for rotation in a frame 20, as illustrated schematically in FIG. 2. The illustrated embodiment comprises twelve such moulds 1. Each mould 1 has a sievelike bottom 3 which can be moved radially, so as to enable the mould depths to be adjusted. Arranged in the interior of the mould-wheel, radially inwards of each mould, is a circle-segment pressure chamber 4 which in addition to the hub and side-walls of the wheel is also defined by two radially extending walls 5. The wheel side-wall that faces the viewer in FIG. 1 has for each pressure chamber 4 an opening 6.

As illustrated in FIG. 1, the mould-wheel is driven by a drive wheel or pinion 7, and it will be seen from the schematic illustration of FIG. 2 that the wheel hub 9 is mounted for rotation on a fixed shaft 8. Naturally, the wheel can be driven in some other way, for instance by making the shaft rotatable and by connecting the hub 9 to the shaft 8 for co-rotation therewith. The direction of rotation of the wheel is indicated by the arrow A in FIGS. 1 and 3.

Arranged adjacent the wheel side-wall containing the openings 6 is a collecting chamber 10 which is coupled to a source of subpressure (not shown) by means of a conduit 11. This subpressure source may comprise the suction side of a fan or some corresponding device. The side-wall of the collecting chamber that borders on the wheel has a radial extent such as to cover the openings 6. When seen circumferentially, the aforesaid side-wall of the chamber 10 covers five-sixths of the openings 6 provided in the aperture side-wall of the wheel. The remaining sixth part of said openings is covered by the side-wall of a further collecting chamber 12, which is coupled to a source of overpressure (not shown) by means of a conduit 13. The source of overpressure may comprise the exhaust side of the fan whose suction side is connected to the conduit 11, when a fan is used to this end. In the case of the illustrated embodiment, the side-walls of respective collecting chambers 10 and 12 are formed integrally with one another and the chambers are mutually separated by partitioning walls 21.

The side-walls of the chambers 10 and 12 which border on the wheel 2 each have provided therein a respective opening 14 and 15 through which each pressure chamber 4 in the wheel communicates with the collecting chambers as the wheel rotates. As seen in the direction of wheel rotation, the overpressure opening 15 is located immediately behind the central symmetry line of the opening 6 of a pressure chamber whose peripheral part is connected with the mould which deposits a formed abosorption body on a conveyer path W, as described in more detail below. When seen radially, the opening 15 has an extent such that in the absorption-body outfeed position the opening will cover the major part of the corresponding opening 6 of the pressure chamber concerned, whereas the circumferential width of the opening corresponds approximately to the width of the opening 6. The opening 14, on the other hand, extends circumferentially over the major part of the pertinent side-wall of the collecting chamber 10 and has a size which varies radially, as will be described in more detail herebelow.

In the case of the illustrated embodiment, the side-walls of respective collecting chambers 10 and 12 have the form of discs, this configuration facilitating the exchange of the disc which contains the openings 14 and 15, so as to enable this side-wall to be replaced with another.

The illustrated apparatus also includes an inlet chamber 16 which extends around a part of the wheel circumference and through which a homogenous mixture of air and cellulose-fibres, or some corresponding material, is introduced into the moulds. This inlet chamber is connected to a device 22 in which it is ensured that the airborne fibres are in homogenous mixture at the outlet of said device.

Certain of the abovementioned apparatus components will be described in more detail in conjunction with the following description of the modus operandi of the apparatus just described, with particular reference to FIG. 3, which illustrates the preferred configuration of the openings 14 and 15.

Figure 3:
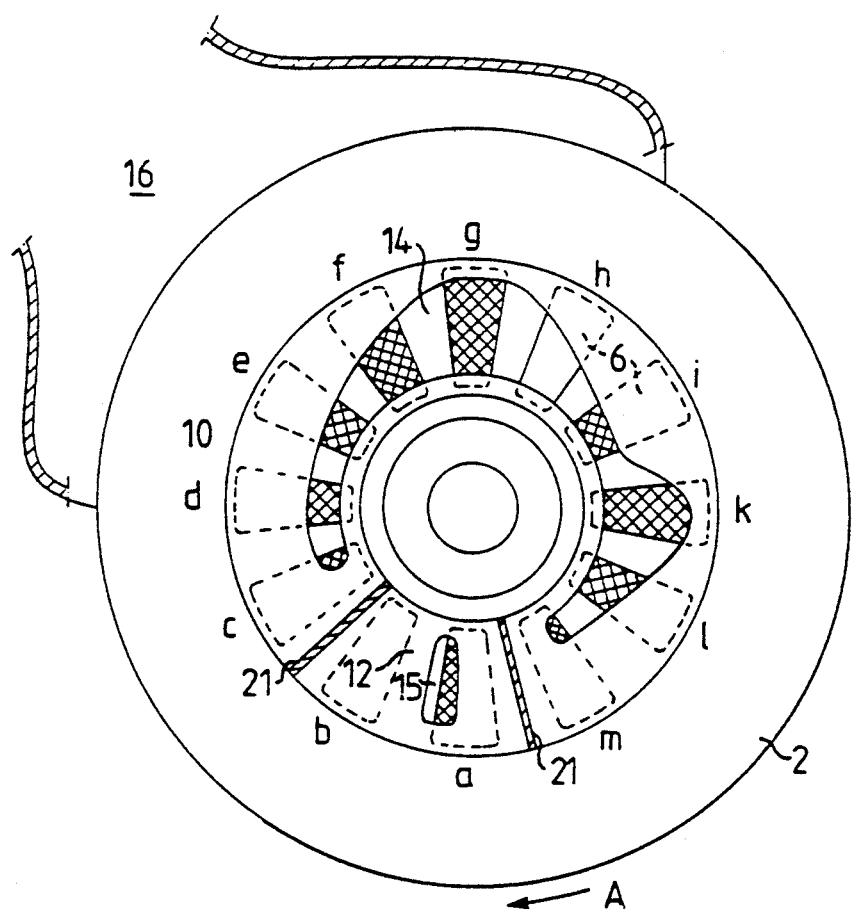
FIG. 3 is a sectional view taken on the line III—III in FIG. 2.

In FIG. 3, the reference letters a-m indicate the various positions occupied by the opening 6 of the respective pressure chamber 4 when one of the moulds is located immediately opposite a continuously moving conveyer path W. For the purpose of describing the various stages of manufacture of an absorption body, the mould which is shown located in said outfeed position and which thus deposits its absorption body on the path W (FIGS. 1 and 2) will be followed during travel of the mould through one revolution of the wheel 2.

As the mold concerned rotates between position a and b, communication between the collecting chamber 12 and pressure chamber 4 (the partition walls 5 defining the pressure chambers are not shown in FIG. 3 for the sake of clarity) is interrupted when the overpressure opening 15 no longer overlaps the pertinent opening 6 in the wheel side-wall. During this part of said revolution, the pressure chamber 4 located beneath the mold concerned communicates with the ambient atmosphere through the mould bottom, and consequently the pressure in the pressure chamber will equal atmospheric pressure as soon as the opening 6 has completely passed the overpressure opening 15.

During its movement between the positions b and c, the mould leaves the region of the collecting chamber 12 and enters the region of the collecting chamber 10. At the end of this movement, the leading part of the opening 14 will slightly overlap the pressure-chamber opening 6 and a slight subpressure will be created in the pressure chamber, due to the fact that as a result of the small overlap in this position the through-flow opening from the collecting chamber 10 to the pressure chamber will be very small and consequently the pressure drop over the through-flow opening in position c will be very large. The through-flow area through which the collecting chamber 10 communicates with the various pressure chambers in positions a-m has been cross in FIG. 3.

Rotation of the mould between the positions c and d will cause the subpressure opening 14 to overlap the pressure-chamber opening 6 in a circumferential direction, to a successively increasing extent. A progressively larger subpressure, i.e. a progressively smaller pressure, will be generated in rhythm with the decrease in the pressure drop over the connection between the collecting chamber 10 and the pressure chamber 4, this connection consisting of the overlapping parts of the openings 14 and 16. In position d, the pressure chamber 4 will have passed the position in which the opening 6 completely overlaps the opening 14 in the circumferential direction. During its movement between positions c and d, the mould 1 is, at the same time, located with the region of the inlet chamber 16, and as a result of the subpressure prevailing in the pressure chamber 4 a mixture of air and cellulose-fibres will be drawn into the mould, where from the air passes through the permeable mould-bottom and into the pressure chamber and exits through the conduit 11, via the collecting chamber, while depositing said fibres on the mould bottom.

As shown in FIG. 3, the radial width of the opening 14 increases proressively between the positions d and g, and at position g has reached a size such that, in this position, the opening 6 is overlapped almost completely by the opening 14 in the radial direction. It will therefore be seen that the pressure drop over the connection between collecting chamber and pressure chamber will decrease progressively during passage of the pressure chamber between the positions d and g.

This compensates the increase in pressure drop which occurs because the air in the air/fibre mixture drawn into the mould 1 during this part of wheel rotation passes through a growing layer of deposited fibres, in addition to passing through the mould bottom. Thus, by appropriate configuration of the opening 14, the subpressure in the pressure chamber can be used to develop to an extent such that the air-flow through the mould bottom will be substantially constant. Provided that the fibre content of the air-fibre mixture flowing into the mould is homogeneous, i.e. uniform in quantity and distribution, the mould will thus be filled uniformly with a constant quantity of fibres per unit of time.

In the case of known apparatus of the kind mentioned in the introduction, the mould bottoms discharge into a pressure chamber which is common to all moulds and which is connected to a source of subpressure. Consequently, the air-flow through an empty mould will be very high and a large quantity of fibres will be deposited in the initial stage of the mould-filling process. The fluff mass nearest the mould bottom will therefore be relatively compact and the resistance to air flow through the mould will thus increase markedly at the beginning of a mould-filling process, whereafter the increase in resistance becomes successively lower as the airflow through the mould successively decreases, due to the increasing pressure drop over the mould. An absorption body which is formed in this manner will increase in density in a direction from the upper edge of the mould to the mould bottom.

The arrangement of a separate pressure chamber beneath each mould bottom and the creation of a varying pressure-drop over the connection between each pressure chamber and the subpressure source, as achieved in accordance with the present invention, will result in a relatively small subpressure in respective pressure chambers at the beginning of the mould-filling process. If this subpressure is increased in rhythm with the rate at which the mould is filled, the increase in pressure drop over the mould can be compensated for by increasing the pressure drop over the connection between pressure chamber and collecting chamber. Thus, with appropriate configuration of the opening 14, these successive changes in pressure drop will cancel each other out, so that the air-flow through the mould, and therewith through the chamber, can be held constant. As a result, the fluff mass deposited in the mould will be compressed to a uniform degree of compaction, resulting finally in a homogenous absorption body which has uniform density throughout.

When the air-flow through the mould is constant, the air-flow resistance over the mould will increase proportionally to the extent to which the mould is filled, since under conditions such as these the density of the fluff-mass is constant. Consequently, in this case the pressure drop which develops linearly over the mould shall be compensated by a linearly decreasing pressure-drop over the connection between the collecting chamber 10 and each pressure chamber 4 during its rotational travel between the positions c and g. The radial width of the opening 14 during this part of its extension can therefore be determined experimentally with relative ease.

When the mould reached position g, in which the subpressure is at a maximum, filling of the mould is complete, in principle. Between the positions g and m, the subpressure need only be sufficiently large to ensure that the fluff mass will be held securely in the mould and the radial width of the opening 14 can be greatly reduced. The radial width of the opening 14 is preferably not decreased abruptly, since abrupt changes can result in disturbances in the air flow with resultant disturbances in the form of eddy current, turbulene or the like.

The reference numeral 17 in FIG. 1 identifies a rotating brush which is operative to remove surplus fluff-mass from the formed absorption body, and in a corresponding position k in FIG. 3 the radial width of the opening 14 has increased almost to its maximum, so as to ensure that the absorption body present in the mould will not be disturbed by the action of the brush 17.

As illustrated schematically in FIG. 1, the apparatus includes roller arrangement 18 which functions to smooth the upper surface of the absorption body in said mould, prior to brushing-away surplus fluff. This arrangement can be omitted when it is certain that the airfibre mixture in the inlet chamber 16 will actually be 100% homogeneous.

In the position m, the pressure drop over the openings 14 and 6 is very large and consequently the pressure then prevailing in the pressure chamber will be closed to atmospheric pressure.

During its rotation between the positions m and a, the mould leaves the region of the collecting chamber 10 and enters the region of the collecting chamber 12. When the pressure-chamber opening 6 is no longer overlapped by the opening 14, atmospheric pressure will prevail in the pressure chamber until the opening 6 is connected with the opening 15, whereafter an overpressure is quickly generated in the pressure chamber, such as to press the formed absorption body from the mould 1 and down onto the conveyer path W. Maximum overpressure is reached in the pressure chamber at the beginning of its rotational movement between the positions a and b. The opening 15 is located behind the symmetry line of the opening 6 of the pressure chamber in position a, in order to prevent the absorption body being deposited onto the conveyer path W before said body is located in the closest possible position in relation to said path.

The aforedescribed filling process is repeated upon continued rotation of the wheel.

Although the subpressure control has been described with reference to the production of homogenous absorption bodies, it will be understood that this control can also be employed in the production of absorption bodies whose densities vary in the direction of their thicknesses, by changing the configuration of the opening 14. This can be readily achieved in the case of the described apparatus, by simply replacing the disc containing the openings 14 and 15 with another disc containing openings 14 of another configuration.

Furthermore, the invention can also be used for filling moulds which move along a linear path instead of a circular path, without changing the constructive, basic principles of the subpressure control.

Thus, the invention provides, with the aid of simple means, a method and apparatus with which homogenous absorption bodies can be produced.

It will be understood that it lies within the scope of the invention to effect control of the subpressure in some way other than by means of the inventive apparatus, for instance by controlling the speed of a fan, and the described and illustrated arrangement merely constitutes a preferred embodiment. The invention is therefore only restricted by the scope of the following claims.

I claim:

1. In a method of forming an absorption body in which a mold having an air-permeable bottom is filled progressively with airborne fibers of absorbent material and in which subpressure is applied through the air-permeable mold bottom; the improvement comprising varying said subpressure progressively and directly as the thickness of the absorption body progressively increases as the mold is progressively filled with said fibers, such that the amount of air drawn through said absorption body by said subpressure remains substantially constant despite progressive increase in the thickness of said body, thereby to produce an absorption body having substantially constant density throughout its thickness.

2. A method as claimed in claim 1, and moving said absorption body in one direction along a path of movement during said progressive filling of the mold, and progressively increasing in said one direction the subpressure to which the interior of said mold is subjected.

3. A method as claimed in claim 2, and maintaining the subpressure to which the interior of the mold is subjected, substantially constant across the width of said absorption body in a direction perpendicular to said one direction, at any point along said path of movement of said absorption body.

4. Apparatus for forming an absorption body, comprising a mold having an air-permeable bottom, means for progressively supplying a mixture of air and loose fibers to the interior of the mold, means for creating a subpressure in the mold, and means for varying said subpressure progressively as the thickness of fibers in the mold progressively increases, said varying means progressively increasing said subpressure as said thickness progressively increases.

5. Apparatus as claimed in claim 4, and means for moving the mold in one direction along a path of movement while progressively depositing fibers in the mold, said means for varying the subpressure progressively increasing the subpressure as the mold moves along said path of movement in said one direction.

6. Apparatus as claimed in claim 5, said means for varying the subpressure maintaining subpressure substantially constant across the width of the absorbent body in a direction perpendicular to said one direction, at any point along said path of movement.

7. Apparatus as claimed in claim 5, said means for progressively increasing the subpressure comprising a chamber communicating with the bottom of the mold on the side of the bottom of the mold opposite the fibers, said chamber moving along said path of movement, and means establishing communication between said chamber and a source of vacuum through an opening which progressively increases in size along said path of movement.

8. Apparatus as claimed in claim 7, wherein said opening is defined between side edges spaced a progressively greater distance apart in said one direction along said path of movement.

9. Apparatus as claimed in claim 8, said means for moving said mold along said path of movement comprising a rotatable wheel on which said mold and chamber are mounted, said opening being formed in a stationary member and extending arcuately about a portion of the circumference of said wheel.

10. Apparatus as claimed in claim 9, wherein said member is a replaceable plate, thereby to permit adjustment of the size and shape of said opening.

* * * * *